United States Patent [19]

Lieberman et al.

[11] Patent Number: 5,002,936

[45] Date of Patent: * Mar. 26, 1991

[54] LIPOPHILIC COMPLEXES OF PHARMACOLOGICALLY ACTIVE INORGANIC MINERAL ACID ESTERS OF ORGANIC COMPOUNDS

[76] Inventors: Seymour Lieberman, 32-22 163 St., Flushing, N.Y. 11358; V. V. K. Prasad, 20 W. 84th St., Apt. 4B, New York, N.Y. 10023; Laura Ponticorvo, 454 Greenmont Ave., Cliffside Park, N.J. 07010

[ * ] Notice: The portion of the term of this patent subsequent to Oct. 25, 2005 has been disclaimed.

[21] Appl. No.: 261,673

[22] Filed: Oct. 24, 1988

Related U.S. Application Data

[63] Continuation-in-part of Ser. No. 722,735, Apr. 12, 1985, Pat. No. 4,780,455.

[51] Int. Cl.$^5$ .................. A61K 31/685; A61K 31/56; C07J 9/00
[52] U.S. Cl. .................. 514/77; 514/78; 514/152; 514/169; 514/170; 514/182; 514/282; 514/64; 260/397.2; 556/606; 556/544; 556/607; 556/636; 556/505; 556/506
[58] Field of Search .................. 514/77, 78, 152, 169, 514/170, 182, 282; 260/397.2; 424/83

[56] References Cited

U.S. PATENT DOCUMENTS

| | | | |
|---|---|---|---|
| 3,919,430 | 11/1975 | Siegel | 424/365 |
| 3,934,013 | 1/1976 | Poulsen | 424/239 |
| 4,158,707 | 6/1979 | Steffan et al. | 424/244 |
| 4,248,867 | 2/1981 | Ikushima et al. | 424/236 |
| 4,780,455 | 10/1988 | Lieberman et al. | 514/77 |

OTHER PUBLICATIONS

Burstein, S., Biochim. Biophys. Acta, vol. 62, pp. 576–578 (1962).
Burstein, S. and Dorfman, R. I., J. Biol. Chem., vol. 238, pp. 1656–1660 (1963).
Le Grimellec, C., et al., Lipids, vol. 19, No. 6, pp. 474–477 (1984).

*Primary Examiner*—Merrell C. Cashion, Jr.
*Assistant Examiner*—Carlos Azpuru

[57] ABSTRACT

The present invention provides a composition with the structure $$(L)_m (E)_n$$

wherein $(L)_m$ and $(E)_n$ are bound as a complex, wherein L is a lipophilic compound; wherein E is a nonlipophilic, ionic, inorganic ester of an organic compound; and wherein m and n are each integers which may be the same or different.

32 Claims, No Drawings

LIPOPHILIC COMPLEXES OF PHARMACOLOGICALLY ACTIVE INORGANIC MINERAL ACID ESTERS OF ORGANIC COMPOUNDS

This application is a continuation-in-part of U.S. Ser. No. 722,735, filed Apr. 12, 1985, now U.S. Pat. No. 4,780,455, issued Oct. 25, 1988, the contents of which are hereby incorporated by reference into this application.

BACKGROUND OF THE INVENTION

The present invention relates to novel compositions of non-lipophilic, ionic, inorganic esters of organic compounds. The inventive compositions are useful, for example, for altering the solubility properties of the esters and for providing controlled-delivery systems for pharmaceuticals.

Frequently a physical property of a chemical must be altered to enable its purification or chemical manipulation. This is often accomplished by chemically modifying a functional group on the molecule. For example, an organic acid may be esterified to render it lipid-soluble, or volatile. A primary difficulty with such chemical modifications of biologically important compounds, such as pharmaceuticals, is that the functional group sought to be altered is often involved in the particular compound's biological activity. Thus, changing the compound's structure can destroy its essential biological activity. Accordingly, the search for methods of altering the physical properties of compounds of interest without altering the chemical structure of the compounds is the subject of active and ongoing research.

Such methods for solubilizing lipophilic compounds in water are known. One of these is the creation of dispersible lipid vesicles or micelles into which lipophilic compounds of interest can be incorporated. For example, Steffan, U.S. Pat. No. 4,158,707 discloses the use of micelles comprising cholic acid and certain lipoids as aqueous vehicles suitable for parenteral administration of medicaments which are insoluble in water. These methods require the careful creation of suitable micelled, detailed knowledge of the extent to which the medicament can be incorporated into the micelles and the physical separation of micelles from the unincorporated material.

Certain limited methods for creating lipophilic complexes of non-lipophilic materials also are available. Thus, lipophilic crown ether complexes of metal ions are known, but crown ether complexes of larger, organic molecules do not exist. Development of lipophilic complexes of such non-lipophilic compounds would be highly desirable, and is an object of the present invention.

A further object of this invention relates to the controlled administration of pharmaceuticals, which is often necessary to insure their maximum effectiveness with a minimum of side effects. The concentration of a drug at the target site may be manipulated by many controlled release means, as described in Benson et al., (1982), Pharmaceuticals, Controlled Release, *Encyclopedia of Chemical Technology* 17, pp. 290–310. Some of these means maintain the concentration of a drug in the bloodstream at a constant level, while others serve to release the drug only to certain organs or tissues. The methods include, for example, delivery modules from which the drug is slowly leached, intravenous drip systems, complex mini-pumping systems placed within the body, and liposome delivery systems. The particular system chosen for delivery of a given pharmaceutical depends upon many factors including the specificity or generality of the drug's site of action, the concentration needed for therapeutic effectiveness, the precision with which a given concentration of the drug must be maintained, and the length of time the optimal dose level must persist. Also important are properties of the pharmaceutical itself such as its solubility properties and its stability once released into the bloodstream or tissue. Clearly, modification of the properties of a pharmaceutically effective compound so that it can be administered by a wider range of controlled delivery systems would greatly increase the therapeutic usefulness of the drug.

The present invention provides novel compositions of a lipophilic compound with a non-lipophilic, ionic, inorganic ester of an organic compound.

The present invention also provides a composition of a non-lipophilic ionic inorganic ester of an organic compound, the compound having solubility properties which differ from the solubility properties of the ester.

Another embodiment of the present invention provides pharmaceutically effective compositions comprising the novel compounds of interest.

SUMMARY OF THE INVENTION

The present invention provides a composition with the structure $$(L)_m(E)_n$$

wherein and $(L)_m$ and $(E)_n$ are bound as a complex. wherein L is a lipophilic compound; wherein E is a nonlipophilic, ionic, inorganic ester of an organic compound; and wherein m and n are each integers which may be the same or different.

In the inventive compositions, the values of m and n are variable and depend upon the manner in which the compositions are made.

The component referred to as "L" is a lipophilic compound which can be selected from the group consisting of phospholipids, cardiolipins, distearins, and tristearins.

The component of the inventive composition referred to as "E" is a non-lipophilic, ionic, inorganic ester of an organic compound. Preferred esters are phosphates, phosphonates, borates, nitrates and sulfates. Typical esters are derivatives of organic compounds. Such organic compounds include steroids, analgesics, antibiotics, antiviral drugs, castanospermine, anticancer agents, antihypertensive drugs, or drugs used in the treatment of heart disease.

The present invention provides compositions, including pharmaceutically acceptable compositions, containing inventive compositions which are pharmaceutically effective. These compositions may be in the form of any of the wide variety of pharmaceutically effective compositions known to the pharmaceutical industry, including pastes, solids, liquids, oily suspensions, powders, pills and capsules.

The present invention provides for a lipophilic composition comprising a phospholipid bound as a complex to a non-lipophilic, ionic, sulfate of an organic compound.

DETAILED DESCRIPTION OF THE INVENTION

The present invention provides a composition with the structure $$(L)_m (E)_n$$

wherein $(L)_m$ and $(E)_n$ are bound as a complex, wherein L is a lipophilic compound; wherein E is a nonlipophilic, ionic, inorganic ester of an organic compound; and wherein m and n are each integers which may be the same or different.

In the inventive compositions, the values of m and n are variable and depend upon the manner in which the compositions are made. Factors likely to influence the values of m and n are the solvents used to dissolve the compound, the precise chemical structures of L and E, and the concentration of the compound. Thus, the values of m and n can vary from about 1 to about one million or more. The ratio of m and n ranges from about 0.01 to about 100. The ratio of m and n is typically between about 0.1 to about 10, e.g. about 1:1. It is entirely possible that a composition of this invention will comprise a mixture of complexes of differing overall sizes and differing ratios of m and n.

The component of the inventive compositions referred to as "L" is a lipophilic compound which can be selected from the group consisting of phospholipids, cardiolipins, distearins, and tristearins. In one preferred embodiment L is the phospholipid phosphatidylethanolamine.

The component of the inventive composition referred to as "E" is a non-lipophilic, ionic, inorganic ester of an organic compound. Preferred esters are phosphates, phosphonates, borate, nitrates and sulfates. Typical esters are derivatives of organic compounds. The organic compound may be a steroid or a substituted steroid, such as a sterol or substituted sterol including cholesterol. Other preferred steroids are steroid hormones including progesterone, pregnenolone, or dehydroepiandrosterone. Another preferred organic compound is an analgesic, such as a narcotic alkaloid. The narcotic alkaloid may be codeine. In this preferred embodiment of the invention, the ester is a sulfate ester of codeine.

The organic compound may also be an antibiotic. The antibiotic may be a modified napththacene molecule such as tetracycline. In this preferred embodiment of the invention, the ester is a sulfate ester of tetracycline. The organic compound of preferred embodiments also include antiviral drugs such as 3'-azido-3'-deoxythymidine (AZT) and dideoxycytidine, or the organic compound castanospermine.

The lipophilic composition of the present invention may derive from organic compounds such as anticancer agents, antihypertensive drugs, and drugs used in the treatment of heart disease. Typical anticancer agents of the preferred embodiments include antibiotic derivatives such as doxorubicin hydrochloride, antimetabolites such as fluorouracil, cytotoxic agents such as hydroxyurea capsules, and nitrogen mustard derivatives such as melphalan and megestrol acetate. Typical antihypertensive drugs of the preferred embodiments include spironolactone, prazosin HCl/polythiazide, and hydralazine hydrochloride. Preferred embodiments also derive from drugs used in the treatment of heart disease. These drugs include prophylactic drugs against myocardial infarction such as timolol Maleate/MSD, coronary vasodilator drugs such as isosorbide dinitrate and nitroglycerine, or antianginal preparations such as diltiazem hydrochloride.

The only known limitation on the structure of the organic compounds which can be incorporated into the inventive complexes is that they must be esterifiable with a phosphate, sulfate, borate, nitrate or phosphonate group. Many methods are known to those of ordinary skill in the art of structurally altering the compounds disclosed above without altering the essential function of the compounds; this invention is therefore broadly directed to complexes of nonlipophilic, ionic, inorganic acid esters of organic compounds, and is not intended to be limited to the particular compounds disclosed above.

A further object of the present invention is to provide for pharmaceutical compositions comprising an effective amount of the inventive lipophilic compositions and a pharmaceutically acceptable carrier. These pharmaceutical compositions may be in the form of any of the wide variety of pharmaceutically effective compositions known to the pharmaceutical industry, including pastes, solids, liquids, oily suspensions, powders, pills and capsules. These compositions may contain pharmaceutically acceptable carrier materials such as, for example, starch, gelatin, agar, sugar, carboxymethylcellulose, polyvinylalcohol, magnesium stearate, and sodium alginate. In addition, these preparations may contain other adjuvants and additives known to the art. These compositions may be administered by various means such as subcutaneous pellet or paste, or as an injectible oily suspension.

It is within the scope of this invention to provide compositions suitable for use in animals, humans, bacteria and plants.

The invention provides a means of administering an organic compound to a subject which comprises administering to the subject an effective amount of the pharmaceutical composition of the inventive compositions.

In a preferred embodiment of the invention the lipophilic composition comprises a phospholipid bound as a complex to a non-lipophilic, ionic, sulfate of an organic compound.

This invention is illustrated in the examples which follow. The examples are set forth to aid in understanding of the invention but are not intended to, and should not be construed to limit in any way the invention as set forth in the claims which follow thereafter.

EXAMPLE I

Preparation of Cholesterol Sulfate

Cholesterol sulfate is available commercially or may be prepared as follows.

Cholesterol and sulfurtrioxide-pyridine complex were mixed. To the mixture, NaOH or KOH was then added. The mixture is then poured into an aqueous solution of sodium or potassium carbonate and lyophilized to yield the sodium or potassium salts, respectively.

EXAMPLE II

Preparation of a Lipophilic Complex of Cholesterol Sulfate

One equivalent of cholesterol sulfate was dissolved in methanol-water (9:1, v:v) and extracted with isooctane. Greater than 94% of the sulfate remained in the methanol-water phase. The isooctane layer (upper layer) was discarded. Then one equivalent of phosphatidylethanolamine dissolved in isooctane was added to the sulfate-containing methanol-water preparation. After shaking (to mix the two phases) over 90% of the sulfate was found in the isooctane layer. The isooctane layer was removed, and the isooctane was dried off. The remaining dry material exhibited in the infrared spectrum absorptions characteristic of cholesterol sulfate (about 1220 cm.$^{-1}$), the acyl carbonyls (about 1730 cm.$^{-1}$) and NH stretches (about 3300 cm.$^{-1}$) of the phospholipid.

EXAMPLE II

Preparation of Lipophilic Complex of Cholesterol Sulfate

Cholesterol sulfate is dissolved in chloroform or methanol. To this mixture is added chloroform containing phosphatidylethanolamine. The solvent is then evaporated, and the dry residue solubilized in a nonpolar solvent.

EXAMPLE IV

Solubilization of Sodium Cholesterol Sulfate by an Equimolar Amount of an Additive Tritiated sodium cholesterol sulfate was prepared from tritiated cholesterol (New England Nuclear) by organic synthesis methods known to those of ordinary skill in the art.

A solution of 50 μg of the tritiated sodium cholesterol sulfate in 100 μl methanol was prepared. To aliquots of this solution was added a warm $CHCl_3$ solution of each of the additives listed in Table I. The $CHCl_3$ solution of the additives contained an equivalent molar amount of the additive relative to the amount of cholesterol sulfate. After addition of the additive solution the mixture was taken to dryness under nitrogen. 1.5ml of benzene were added and warmed at 65° C. for ten seconds in a water bath. An aliquot (100 λ) was immediately taken and analyzed by counting the signal emitted from the tritium in a radioactive scintillation counter.

TABLE I

| Additives | Molecular Weight g/mole | Amount Added in μg | Relative[a] Efficiency | Partition Ratio (Value) Max = 1 in 1.5 ml $C_6H_6$ 1.5 ml $H_2O$ |
|---|---|---|---|---|
| | | | 0.0 | |
| Lecithin (Dipalmitoyl phosphatidylcholine) | 734 | 73 | 0.88 | 0.98 |
| Cephalin (dipalmitoyl phosphatidylethanolamine) | 692 | 70 | 0.9 | 0.95 |
| 1,2-dipalmitoyl racemic glycerol | 569 | 56 | 0.02 | 0.30 |
| Cardiolipin | 1200 | 120 | 1.0 | 0.92 |
| Tristearin | 890 | 90 | .01 | 0.50 |

[a]Relative Efficiency is defined as the amount of sterol sulfate solubilized in the lipid phase by the additive relative to the amount solubilized in the lipid phase by the additive cardiolipin. The amount solubilized by the cardiolipin itself is greater than 95% of the maximum.

To determine the partition coefficient a warm benzene solution of the complex (e.g. 1.5 ml) was briefly warmed for approximately 10 seconds in a water bath maintained at 65° C. An equivalent volume of water (e.g. 1.5 ml) warmed to 65° C. was then added and the mixture was shaken. The mixture was then placed in a water bath maintained at approximately 65° C. for approximately 1 minute or until the mixture separated into organic and aqueous layers. Aliquots from both the organic and aqueous layers were taken for analysis, and counted on a scintillation counter.

Results

The lecithin, cephalin and cardiolipin complexes of cholesterol sulfate are lipophilic. The 1,2 dipalmitoyl racemic glycerol and the tristearin complexes with cholesterol sulfate formed in the presence of water also displayed lipophilicity whereas the sodium cholesterol sulfate is insoluble when mixed with 1,2 palmitoyl racemic glycerol or tristearin in an organic solvent. While not wishing to be bound by theory, this effect may be due to a restructuring of the molecular aggregates of the additives in the presence of water such that they create a strong enough hydrophobic core for the steroid nucleus to interact with, which counters the hydrophilicity of the sulfate group.

EXAMPLE V

Comparison of the Partition Ratios of Sodium Cholesterol sulfate complexes, and cholesterol complexes with Different Additives Mixtures of each of the complexes in benzene and water were formed as described above. The mixtures were warmed at 65° C. and shaken as described previously. Aliquots from the organic and aqueous layers were taken and analyzed by detecting the signal emitted from the tritium in a liquid scintillation counter. The results of the comparison of partition ratios are listed in Table II.

TABLE II

| | Partition Ratio[a] Max = 1 | |
|---|---|---|
| Additive | Sodium Cholesterol Sulfate | Cholesterol |
| Lecithin | 0.98 | 0.85 |
| Chephalin | 0.95 | 0.85 |
| 1,2 dipalmitoyl racemic glycerol | 0.30 | 1.0 |
| Cardiolipin | 0.92 | 0.98 |
| Tristearin | 0.50 | 1.0 |

[a] $\frac{\text{cpm in upper phase}}{\text{cpm in upper phase + cpm in lower phase}}$;
cpm = counts per minute

EXAMPLE VI

Experiments to Test Time Delayed Metabolic Clearance Rate of Steroid Sulfate-Phospholipid Complex Pairs of rats (Wistar) were injected subcutaneously with uncomplexed ($^3$H)-dehydroandrosterone sodium sulfate and with a 1:1 phospholipid (dipalmitoylphosphatidylethanolamine) complex of the steroid sulfate. As a control, a 1:1 complex of the phospholipid and underivatized steroid, dehydroandrosterone (DHA) was also administered to a fifth rat. Feces and urine were collected at 24 h, 48 h and 120 h. Excreta at each time period were combined with 200 ml of methanol and blended for 30 seconds. The methanol extracts were filtered and aliquots counted for radioactivity.

Results: The underivatized steroid (DHA)-phospholipid mixture at all measured intervals showed a metabolic clearance rate that was twice as fast as that of the uncomplexed steroid sodium sulfate. Initially (24 h) no significant difference between the uncomplexed and complexed sulfate salts was observed. At the latter two time points (48 h, 120 h), however, the phospholipid complex of the steroid sodium sulfate was metabolically cleared at a rate 25–30% slower than the uncomplexed steroid sulfate.

EXAMPLE VII

Lipid-Soluble Complex of the Sulfuric Acid Ester of Tetracycline with Phosphatidylethanolamine 500 mg tetracycline was dissolved in 3 cc tetrahydrofuran. The solution was diluted with 100 cc of ether and then 1 cc pyridine was added. Sulfation was accomplished by adding 1 cc of chlorosulfonic acid. After 15 min the solvent was evaporated and the saturated solution of sodium chloride was added to the residue. The precipitate which formed was filtered, dried, and recrystallized from methanol containing water. The tar-like precipitate had the following properties: it was soluble in water, methanol, acetone, chloroform; it was slightly soluble in benzene and it was insoluble in hexane and cyclohexane. It formed an insoluble salt with mercuric chloride and slowly formed a precipitate with calcium ions and magnesium ions.

A small amount of the sulfate was suspended in chloroform and to it a suspension of phosphatidylethanolamine in chloroform was added. The solvent was evaporated to dryness. The yellow residue was found to be soluble in hexane and cyclohexane.

This experiment proves that the sulfuric acid esters of tetracycline which itself is insoluble in hexane and cyclohexane have been converted by complexation with phosphatidylethanolamine into a complex which is soluble in a non-polar solvent like hexane.

EXAMPLE VIII

Lipid-Soluble Complex of the Sulfuric Acid Ester of Codeine with Phosphatidylethanolamine 400 mg of codeine was dissolved in 55 cc of ether. To the solution was added 0.3 cc pyridine dissolved in 25 cc of ether. 0.2 cc of chlorosulfonic acid was then added to the mixture. After standing overnight the volatile solvents were removed by evaporation. Sodium chloride solution was added. Since no precipitate formed, the solution was evaporated to dryness. The residue was extracted with methanol leaving behind the insoluble NaCl. The methanolic extract was evaporated to dryness leaving the sulfate as an oily residue. The residue had the following properties: insoluble in hexane, cyclohexane and benzene; soluble in methanol. It had UV absorption maximum at 354 nm in methanol.

An aliquot of the oily sulfate was treated with phosphatidylethanolamine suspended in chloroform. The suspension was taken to dryness and then the dry residue was extracted into hexane. The hexane solution exhibited an absorption spectrum maximum at 253 and 250 nm in methanol.

This experiment proves that codeine sulfate which is insoluble in hexane and cyclohexane has been converted by treatment with phosphatidylethanolamine into a lipophilic complex.

This invention concerns a drug delivery system that has wide applications. Not only does this invention provide a novel means of delivery for steroids, antibiotics and analgesics, as the examples herein illustrate, it can be employed for antiviral drugs such as AZT and dideoxycytidine, trimming agents like castanospermine, anticancer agents, and drugs used in the treatment of hypertension and diseases of the heart.

What is claimed is:

1. A lipophilic composition having the formula:

$$(L)_m (E)_n$$

wherein $(L)_m$ and $(E)_n$ are bound as a complex, wherein L is a lipophilic compound; wherein E is a non-lipophilic, ionic, inorganic mineral acid ester of an organic compound; and wherein m and n are each integers which may be the same or different.

2. A lipophilic composition of claim 1, wherein L is selected from the group consisting of phospholipids, cardiolipins, distearins, and tristearins.

3. A lipophilic composition of claim 1, wherein L is a phopholipid.

4. A lipophilic composition of claim 3, wherein the phospholipid is phosphatidylethanolamine.

5. A lipophilic composition of claim 1, wherein the inorganic mineral acid ester is a phosphate, sulfate, borate, nitrate or phosphonate.

6. A lipophilic composition of claim 5, wherein the inorganic mineral acid ester is a sulfate.

7. A composition according to claim 1, wherein the organic compound is a steroid or a substituted steroid.

8. A composition according to claim 7, wherein the steroid is a sterol or a substituted sterol.

9. A composition according to claim 8, wherein the sterol is cholesterol.

10. A composition according to claim 7, wherein the steroid is a steroid hormone.

11. A composition according to claim 10, wherein the steroid hormone is progesterone, pregnenolone, or dehydroepiandrosterone.

12. A composition according to claim 1, wherein the organic compound is an analgesic.

13. A composition according to claim 12, wherein the analgesic is a narcotic alkaloid.

14. A composition according to claim 13, wherein the narcotic alkaloid is codeine.

15. A composition according to claim 1, wherein the ester is a sulfate ester of codeine.

16. A composition according to claim 1, wherein the organic compound is an antibiotic.

17. A composition according to claim 16, wherein the antibiotic is a modified napththacene molecule.

18. A composition according to claim 17, wherein the modified napththacene molecule is tetracycline.

19. A composition according to claim 1, wherein the ester is a sulfate ester of tetracycline.

20. A composition according to claim wherein the organic compound is an antiviral drug.

21. A composition according to claim 20, wherein the antiviral drug is 3'-azido-3'-deoxythymidine (AZT).

22. A composition according to claim 20, wherein the antiviral drug is dideoxycytidine.

23. A composition according to claim 1, wherein the organic compound is castanospermine.

24. A composition according to claim 1, wherein the organic compound is an anticancer agent.

25. A composition according to claim 1, wherein the organic compound is an antihypertensive drug.

26. A composition according to claim 1, wherein the organic compound is a drug used in the treatment of heart disease.

27. A composition according to claim 1, wherein the ratio of m to n is from about 0.01 to about 100.

28. A composition according to claim 27, wherein the ratio of m to n is from about 0.1 to about 10.

29. A composition according to claim 27, wherein the ratio of m to n is about 1:1.

30. A pharmaceutical composition comprising an effective amount of a composition of claim 1 and a pharmaceutically acceptable carrier.

31. A method of administering an organic compound to a subject which comprises administering to the subject an effective amount of the pharmaceutical composition of claim 30.

32. A lipophilic composition comprising a phospholipid bound as a complex to a non-lipophilic, ionic, sulfate of an organic compound.

* * * * *